United States Patent [19]
Jeon et al.

[11] Patent Number: 6,082,179
[45] Date of Patent: Jul. 4, 2000

[54] PARTICLE MEASURING DEVICE HAVING FUNNEL-SHAPED COLLECTOR FOR SEMICONDUCTOR CLEAN ROOM APPLICATIONS

[75] Inventors: Jae Kang Jeon; Joung Sun Lee; Jae Heung Choi; Dong Young Kim, all of Kyungki-do, Rep. of Korea

[73] Assignee: Samsung Electronics Co., Ltd., Suwon, Rep. of Korea

[21] Appl. No.: 08/912,431

[22] Filed: Aug. 18, 1997

[30] Foreign Application Priority Data

Aug. 29, 1996 [KR] Rep. of Korea ............... 96-36584

[51] Int. Cl.⁷ .............................. G01N 15/06; G01N 1/24
[52] U.S. Cl. ........................... 73/28.04; 73/863.21
[58] Field of Search ................ 73/28.01, 28.04, 73/863.21, 863.23, 865.5; 95/271

[56] References Cited

U.S. PATENT DOCUMENTS

| | | | |
|---|---|---|---|
| 3,070,990 | 1/1963 | Krinov | 73/28.04 X |
| 3,759,617 | 9/1973 | Barringer | 73/28.01 X |
| 3,780,567 | 12/1973 | Ovard | 73/28.04 X |
| 4,137,751 | 2/1979 | Rhodes et al. | 73/28.04 |

*Primary Examiner*—Michael Brock
*Attorney, Agent, or Firm*—Jones Volentine, L.L.P.

[57] ABSTRACT

A particle measurer used in a semiconductor clean room includes a funnel-shaped collector for facilitating the measurement of a particle level of an air sample in the clean room. The particle measurer is arranged so that a narrow end part of the funnel-shaped collector is connected to an intake of the particle measurer. A wide end of the funnel-shaped connector receives the air sample through a sample air pipe. A pump is used for suctioning the air sample through the intake of said particle counter and for discharging the air sample through an exhaust.

8 Claims, 3 Drawing Sheets

PARTICLE MEASURING DEVICE HAVING FUNNEL-SHAPED COLLECTOR FOR SEMICONDUCTOR CLEAN ROOM APPLICATIONS

BACKGROUND OF THE INVENTION

1. Field of the Invention

The present invention relates to a particle measuring device for measuring dust in semiconductor clean room applications. More particularly, the particle measuring device uses a funnel-shaped collector to concentrate the air sample such that a larger air sample is measured and the sensitivity of the device is improved.

2. Background of the Related Art

A clean room is an interior area with provisions to control and reduce airborne particles to the very low levels required for the manufacture of semiconductors and other such processes. Airborne and suspended particles are controlled so that they cannot reach the object being worked on within the clean room. Also, optimum process conditions for the work object can be obtained by controlling air temperature, humidity and illumination. Measures for preventing noise and vibration are also taken where this will adversely affect the manufacturing process within the clean room.

This is especially true in a semiconductor production line, where a series of processes, such as basic pattern design, layer formation, reticle manufacture, wafer manufacture, inspection, assembly, packaging, final testing, and quality inspections, etc. are executed. During the wafer manufacture process in particular, since exposing, developing, etching and diffusion processes are repeatedly executed, control of dust pollution, temperature and humidity are all very important. These factors are significant to product yield and to the various aspects of improving the precision and reliability of the final products.

Accordingly, pollution management of clean rooms in semiconductor manufacturing processes is very important. In order to properly execute pollution management, it is important to remove dust from the air flowing into the clean room and to prevent pollution sources from being introduced to the clean room. In addition, it is also important to measure the air cleanliness of the clean room, and to manage the clean room by utilizing filtering systems and air conditioning systems on the basis of the measured data.

For pollution management of a clean room, it is necessary to measure the degree of pollution at a position within the actual clean room, using samples taken at various intervals. For this, a particle measuring device is generally used. A suspended particle measuring device is used to measure the cleanliness of the actual clean room from a sample taken from the clean room. Several kinds of suspended clean room from a sample taken from the clean room. Several kinds of suspended particle measuring devices have been variously developed for this purpose and are commercially available.

One such device being used is an optical particle counter for measuring the pollution by measuring the scattering level of a laser beam that occurs from the presence of dust particles in its path. A typical configuration of this device includes a laser light source which generates a laser light beam and a cut-off wall which is installed opposite to the laser light source that cuts off the laser light. In addition, a light sensor is placed perpendicular to the laser beam to measure the light scattered from the laser beam by the airborne dust particles.

Such a conventional particle measuring device is depicted schematically in FIG. 1. A pump 2, having a flow meter 3 attached to one side, is connected to the above-described particle counter 1. The pump 2 circulates fresh air to be measured by the particle counter 1. An entry pipe 5 is also connected to the particle counter 1 to allow the air sample to be drawn therethrough. The air sample is gathered through a directional suction pipe 7, which is connected to the entry pipe 5 by the flexible connection tube 6 at one end. At the other end of the directional suction pipe 7, a wide suction entrance 8 is formed. Therefore, the air sample to be measured is drawn into the entry pipe 5 by the operation of the suction pump 2. Essentially, the particle counter 1 measures the air sample, and the air sample being measured is discharged to the clean-room. In this way, the particle counter 1 measures the quantity of dust particles suspended in the clean room where the air sample was taken.

The particle counter 1, the pump 2 and the flow meter 3 are all known and commercially available, so they will be easily understood to those skilled in this field of technology.

A cleaning filter is placed on the discharge portion of the pump 2, so that additional pollution due to the operation of the particle counter 1 itself does not occur. The connection tube 6 may be a hollow flexible tube made of TEFLON or similar material suitable to this application.

A disadvantage of the conventional particle counter 1 is that it is limited by the size of the air sample to be measured. Since clean rooms are generally getting larger, the relative size of the air sample in comparison with the air contained within the clean room is very small. As a result, the reliability of the measurement decreases.

For example, clean rooms for precision electronics industries, such as a semiconductor production lines, have became larger with heights on the order of 3.5 meters, widths of 100 meters and lengths of 100 meters to facilitate improvements in productivity. Despite circulating the fresh air more than four hundred times per hour to maintain the required high cleanness, the amount of the air sample obtained during one measurement of the particle counter 1 is only 28.3 liters. Note that the measurement sample is $1/_{1.27} \times 10^{-7}$ of the total room volume. It is not very reasonable to manage the whole clean room on the basis of such a small measurement.

On the other hand, although the deviation in measuring data may be reduced by increasing the number of measurements, the amount of the measurement sample is still small in comparison to the total air volume of the whole clean room. Furthermore, the measurement process itself takes considerable time, rendering real time measurements difficult.

Some have tried to increase the sample size so as to decrease the sampling time. But as shown in FIG. 2, there is an inverse relationship between the amount of the measured air sample and the minimum measurable particle diameter. For example, with an ordinary particle counter 1 using a He—Ne laser (helium-neon laser), the minimum measurable particle diameter is only 0.09 μm in the measured sample air of 28.3 liter. Therefore, this second approach is not of much practical use.

SUMMARY OF THE INVENTION

Accordingly, an object of the present invention is to modify a particle measuring device for semiconductor clean room applications where the volume of air to be controlled is large, by adding a funnel-shaped collector in the sample collection piping.

Another object of the present invention is to provide a particle measuring device having a funnel-shaped collector for a semiconductor clean room, capable of measuring particles having a diameter as small as 0.1 μm for a large volume air sample.

It is still another object of the present invention to provide a particle measuring device with an omni-directional suction pipe capable of evenly suctioning the fresh air regardless of the position of the suction pipe.

To achieve these and other objects and advantages of the present invention, there is provided a particle measuring device for measuring particle levels in an air sample of a semiconductor clean room, the device having a particle counter communicating with a pump for suctioning the air sample through an intake means of the particle counter and for discharging the air sample through an exhaust means. The measuring device includes a funnel-shaped collector connected to the intake means. The device is constructed so that the funnel-shaped collector enlarges the volume of the air sample to be measured by being positioned in the sample air intake piping upstream of the particle measuring device.

The funnel-shaped collector is conically shaped with a narrow end part connected to the intake of the particle counter through a connection pipe. The wide end part communicates with the pump with an exhaust pipe. A sample air pipe is connected through the side wall of the wide end part of the funnel-shaped collector.

An omni-directional fitting having a plurality of openings is connected to one end of the sample air pipe. Also, a particle auxiliary pipe has one end connected to the connection pipe and a second end connected to the narrow end part of the funnel-shaped collector. The diameter of the particle auxiliary pipe is sufficient to allow one-half the air sample entering the particle counter to pass through the connection pipe from the narrow end part of the funnel-shaped collector, and another one-half of the air sample to pass through the particle auxiliary pipe.

Since the interior wall of the funnel-shaped collector is electrically polished or treated, dust resident in the air sample does not stick to the interior wall of the funnel-shaped collector.

A speed controller may be attached to the pump for controlling the volume of the sample air introduced into the funnel-shaped collector. The particle measurer can be an optical particle counter utilizing the principal of measuring the amount of light which is scattered by the dust in the air sample which is drawn through the particle counter.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings illustrate embodiments of the invention in which.

DETAILED DESCRIPTION OF PREFERRED EMBODIMENT

Reference will now be made in detail to the preferred embodiments of the present invention, examples of which are illustrated in the accompanying drawings. Note that the term "pipe" as used herein may encompass fixed or rigid pipes as well as flexible pipes or tubes.

Figure 1:
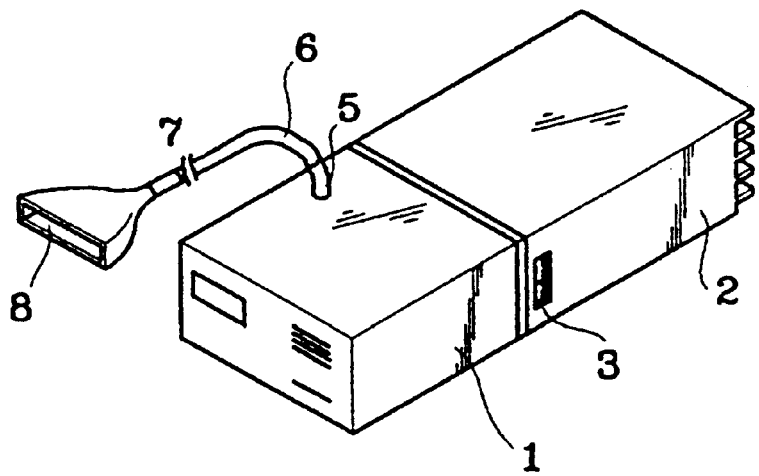
FIG. 1 is a perspective view of a conventional particle measuring device.
Figure 2:
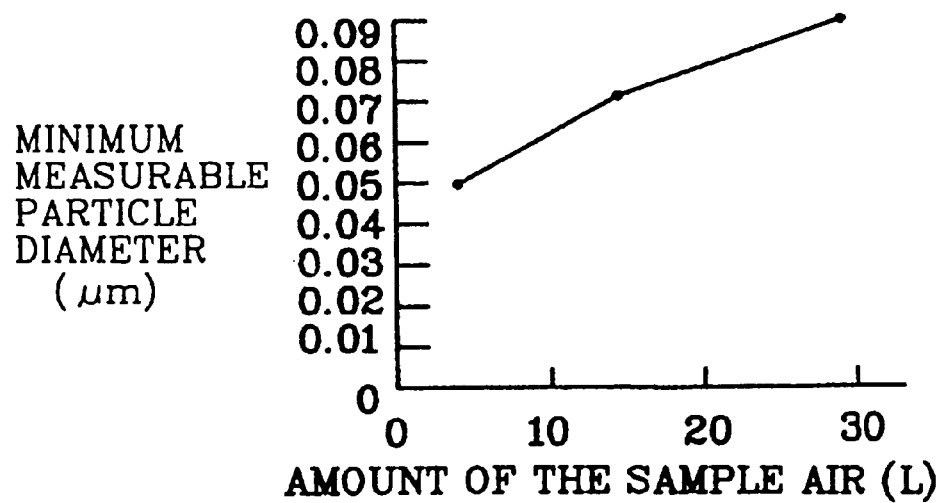
FIG. 2 is a graph showing the relationship between the minimum measurable dust particle diameter to the volume of the air sample.
Figure 3:
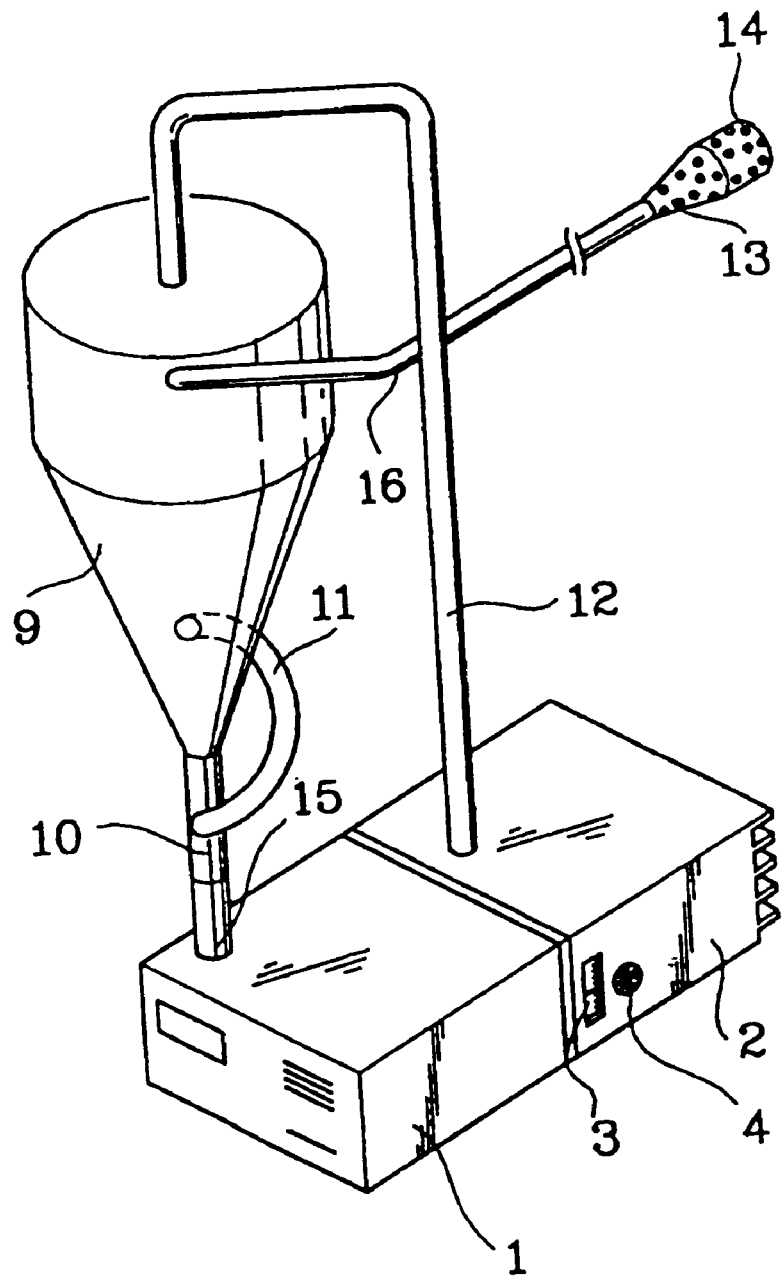
FIG. 3 is a perspective view of the particle measuring device having a funnel-shaped collector for use in semiconductor clean room applications according to the present invention.

As shown in FIG. 3, the particle counter 1 having a funnel-shaped collector 9 according to the present invention includes an air sample intake means 15 and a pump 2 for discharging the measured sample air. The device is characterized by the funnel-shaped collector 9 in order to facilitate capturing a larger volume of the air sample for analysis. The collector 9 is connected to the air sample intake 15 of the particle counter 1. The pump 2 has a cleaning filter and a sample flow meter 3 attached.

In the present invention, instead of simply enlarging the volume of the air sample that would be measured in the conventional particle counter 1, the increase in the volume of the air sample is accomplished by separating dust particles whose weight is heavier than that of air from the air according to the principle of a cyclone. Then, a portion of the concentrated dust particles is sampled as it flows into the particle counter 1 in order to count the number of the dust particles. As a result, despite the increase in the air sample volume, measurements can be made for particles as small as 0.1 μm.

Figure 4:
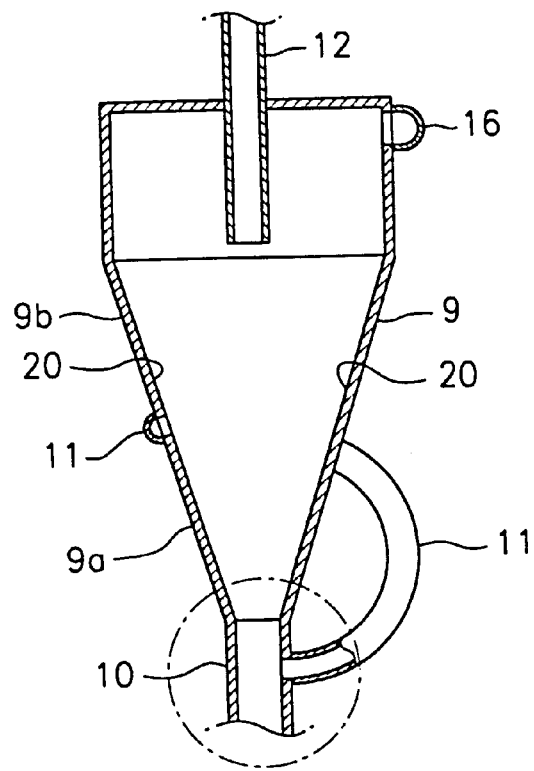
FIG. 4 is a vertical section view showing the funnel-shaped collector of the particle measuring device according to the present invention.
Figure 5:
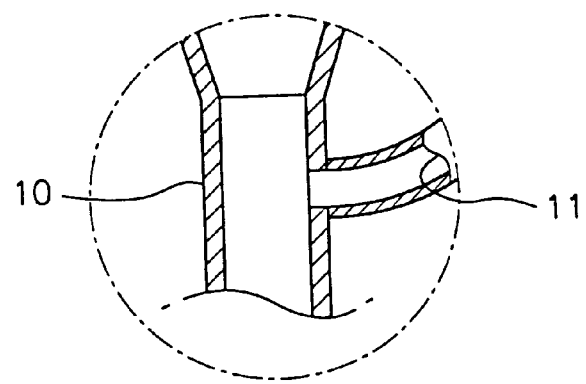
FIG. 5 is an enlarged sectional view of a lower portion of the funnel-shaped collector of FIG. 4.

As shown in FIGS. 3 and 4, the funnel-shaped collector 9 includes a narrow end part 9a and a wide end part 9b. The narrow end part 9a is connected to an intake means or entry pipe 15 of the particle counter 1 through a connection pipe 10. The wide end part 9b is connected to the pump 2 of the particle counter 1 by an exhaust pipe 12. A sample air pipe 16 is connected at one end through a side wall of the wide end part 9b. The funnel-shaped collector 9 is basically a hollow cone shape.

The cyclone principle is described as follows. When fluid within a narrowing cylinder shape is moved in a rotating manner, heavier weight particles within the fluid experience greater centrifugal force and are gradually concentrated at the side of the cylinder shape. In the present invention, air including dust particles is rotated within the funnel-shaped collector 9. The heavier dust particles are acted upon by centrifugal force so that the dust particles are concentrated near the interior wall 20 of the funnel-shaped collector 9.

The interior wall 20 of the funnel-shaped collector 9 can be electrically polished or treated. Electrical polishing is used for smoothing the interior wall by use of electric energy. By heightening the degree of smoothness of the interior wall 20 of the funnel-shaped collector 9 by such a process, air flow resistance within the funnel-shaped collector 9 is minimized. As a result, the suctioning operation of the pump 2 is performed at maximum effectiveness without increasing the power of the pump 2. Also, the adhering of dust particles to the interior wall 20 of the funnel-shaped collector 9 is prevented.

As described above, the connection pipe 10 is simultaneously connected to the intake means 15 of the particle counter 1 and the narrow end part 9a of the funnel-shaped collector 9. The connection pipe 10 channels the air flow from the narrow end part 9a into the particle counter 1 through the intake means 15.

A particle auxiliary pipe 11 can be connected between the narrow end part 9a of the funnel-shaped collector 9 and the connection pipe 10. The particle auxiliary pipe 11 operates so that the dust particles concentrated near the interior wall 20 of the funnel-shaped collector 9 flow along a separate route to the intake means 15 of the particle counter 1. The particles are accompanied by a portion of the air flow from collector 9. Through use of the particle auxiliary pipe 11, the dust particles concentrated by the funnel-shaped collector 9 can be channeled into the particle counter 1 much more effectively.

The exhaust pipe 12, connecting the wide end part 9*b* of the funnel-shaped collector 9 and the pump 2 of the particle counter 1, extends into the central interior portion of the top of the funnel-shaped collector 9. Since the dust particles are subject to centrifugal force and are concentrated near the interior wall 20 of the funnel-shaped collector 9, the air flow at or near the central portion is relatively free of dust particles and is exhausted directly to the pump 2 through the exhaust pipe 12 without going through particle counter 1. Since the air flow from exhaust pipe 12 is discharged through the pump 2, the amount of sampled air flowing through the particle counter 1 is decreased so that the precision of the measurements can be increased, and the minimum measurable particle diameter can be decreased.

The entire volume of air suctioned into the funnel-shaped collector 9 can be approximately divided into halves. About one-half of the air passes through the exhaust pipe 12 and the other half is suctioned directly into the connection pipe 10 from the narrow end part 9*a* of the collector 9. With this arrangement, instead of all the fresh air passing through particle center 1, only a portion passes therethrough. Half of the fresh air, namely the portion in the upper central portion of the wide end part 9*b* in which dust particles are almost absent, does not pass through the particle counter 1 but is discharged directly through pump 2.

The sample air pipe 16 is used for sampling the exterior air and channeling its flow through the side wall of the wide end part 9*b* and into the funnel-shaped collector 9. For this sample air pipe 16, a hollow, flexible pipe fabricated of a synthetic resin material, such as TEFLON, TYGON, etc., can be used.

At the outer end of the sample air pipe 16, a non-directional or omni-directional suction pipe fitting 13 can be used. This fitting 13 has numerous suction holes 14 spaced around it. In contrast to the directional suction pipe 7 used on the end of the connection tube 6 of a conventional particle counter, this omni-directional suction pipe fitting 13 can suction air equally from all directions. This decreases the deviation that occurs due to the inadvertent suctioning of the dust particles attached to the wall of the device when using the conventional directional suction pipe fitting 7. The omni-directional suction pipe fitting 13 can be constructed by forming numerous suction holes 14 on a hollow cylindrical shape. Through these suction holes 14 the fresh air, including the dust particles, is sampled and can flow into the funnel-shaped collector 9 through the sample air pipe 16.

A speed controller 4 can be used on pump 2. The speed controller 4 uses a general variable resistor for controlling the amount of sample air taken into the collector 9. The particle counter 1 can employ a conventional optical particle measuring device for measuring the number of particles by using a laser light source.

The operation of the particle measuring device according to the present invention is as follows.

A fresh air sample flows through the sample air pipe 16 and into the funnel-shaped collector 9 for later measurement by the particle counter 1. The flow is created by the suction force exerted by pump 2 attached to the conventional particle counter 1. This causes air to flow into the funnel-shaped collector 9 and then to the particle counter 1 via the intake means 15 and the connection pipe 10.

The air flow around the inside of the wide end part 9*b* of the funnel-shaped collector 9 is accelerated when the air flows downwardly in the collector 9 since the lower portion of the collector 9 is progressively narrower. As the air flows to the narrow end part 9*a* of the collector 9, it causes air rotation, either clockwise or counter-clockwise. With the increase in the speed of the air flow, combined with the rotating movement, the heavier dust particles resident in the air flow are subjected to a greater centrifugal force. As a result, the dust is concentrated near the interior wall 20 of the funnel-shaped collector 9. Consequently, the dust particles are relatively absent from the central portion of the wide end part 9*b* of the funnel-shaped collector 9.

This air near the central portion of the wide end part 9*b*, comprising about one-half the volume of the original air sample, flows into the pump 2 through the exhaust pipe 12, without passing through the particle counter 1, and is thereafter discharged from the pump 2.

The remaining portion of the air sample flows downwardly through the collector 9. The dust particles concentrated at or near the interior wall 20 of the funnel-shaped collector 9 flow into the connection pipe 10 through the particle auxiliary pipe 11 together with portion of the remaining air flow. Meanwhile, the rest of the air in the collector 9 flows into the particle counter 1 through the connection pipe 10.

Preferably, the diameter of the particle auxiliary pipe 11 is sufficient to allow about one-half the air sample entering said particle counter to pass through said connection pipe 10 from the narrow end part 9*a* of the funnel-shaped collector 9, and another one-half of the air sample to pass through the particle auxiliary pipe 11.

With the present invention, the funnel-shaped collector 9 attached to the particle measuring devices 1 captures a great deal of fresh air, concentrates the dust particles resident in the fresh air, and forces the dust particles to flow into particle counter 1 together with a smaller portion of the fresh air so as to count the number of the dust particles. Meanwhile, the rest of the fresh air is directly discharged through the pump 2 without passing through the particle counter 1. Thus, the funnel-shaped collector 9 carries out the role of concentrating dust particles.

Furthermore, by concentrating the dust particles using this apparatus, it is possible to make accurate measurements for amounts of air as small as those which where sampled and measured in existing particle measuring devices, but without raising the measurable particle diameter associated with particle diameter measurements using large amounts of air. Thus, particle diameters as low as 0.1 $\mu$m can be measured in a short time, providing more reliable measurements.

Also, according to the present invention, the deviation due to the sampling position is small due to the use of omni-directional suction pipe fitting 13.

It will be apparent to those skilled in this art that various modifications and variations can be made in the particle measurer having the funnel-shaped collector for the semi-conductor of the present invention without departing from the spirit or scope of the invention. Therefore, it is intended that the present invention not be limited to the particular embodiment disclosed, but that the present invention include all embodiments falling within the scope of the following claims.

What is claimed is:

1. A particle measuring device for measuring particle levels in an air sample of a semiconductor clean room, said device having a particle counter communicating with a pump for suctioning the air sample through an intake of said particle counter and for discharging the air sample through an exhaust, said measuring device comprising
   a funnel-shaped collector connected to the intake for enlarging a volume of the sample air to be measured, wherein said funnel-shaped collector comprises a narrow end part and a wide end part, said narrow end part being connected to the intake:
   a connection pipe disposed between said narrow end part and the intake; and
   a particle auxiliary pipe having a first end connected to said connection pipe and a second end connected to said narrow end part of said funnel-shaped connector.

2. The particle measuring device as claimed in claim 1, further comprising:
   an exhaust pipe communicating at one end with the wide end part and being connected at another end to the pump.

3. The particle measuring device as claimed in claim 1, further comprising a sample air pipe connected at one end through a side wall of the wide end part of said funnel-shaped collector.

4. The particle measuring device as claimed in claim 3, further comprising an omni-directional suction pipe fitting having a plurality of suction openings being connected to a second end of the sample air pipe for introducing the air sample into said funnel-shaped collector.

5. The particle measuring device as claimed in claim 1, wherein a diameter of the particle auxiliary pipe is sufficient to allow one-half the air sample entering said particle counter to pass through said connection pipe from the narrow end part of the funnel-shaped collector, and another one-half of the air sample to pass through the particle auxiliary pipe.

6. The particle measuring device as claimed in claim 1, wherein an interior wall of said funnel-shaped collector is electrically polished-treated.

7. The particle measuring device as claimed in claim 1, further comprising a speed controller attached to the pump for controlling the rate of the air sample introduced into the funnel-shaped collector.

8. The particle measuring device as claimed in claim 1, wherein the particle counter includes an optical particle measurer for measuring the number of particles by using a laser light source.

* * * * *